(12) United States Patent
Li et al.

(10) Patent No.: US 8,236,529 B2
(45) Date of Patent: Aug. 7, 2012

(54) VECTORS, METHODS, SYSTEMS AND KITS FOR PROTEIN PURIFICATION

(75) Inventors: Yaw-Kuen Li, Hsinchu (TW); Yue-Jin Wu, Mailiao Township, Yunlin County (TW)

(73) Assignee: National Chiao Tung University, Hsinchu (TW)

( * ) Notice: Subject to any disclaimer, the term of this patent is extended or adjusted under 35 U.S.C. 154(b) by 350 days.

(21) Appl. No.: 12/641,757

(22) Filed: Dec. 18, 2009

(65) Prior Publication Data

US 2011/0151514 A1 Jun. 23, 2011

(51) Int. Cl.
- *C12P 21/00* (2006.01)
- *C12N 15/63* (2006.01)
- *C12N 1/21* (2006.01)

(52) U.S. Cl. ............... 435/69.7; 435/252.33; 435/320.1

(58) Field of Classification Search .................. None
See application file for complete search history.

(56) References Cited

OTHER PUBLICATIONS

Chong et al (Single-column purification of free recombinant proteins using a self-cleavable affinity tag derived from a protein splicing element. Gene. Jun. 19, 1997; 192(2):271-81).*

Bai et al (Improving the oral efficacy of recombinant Granulocyte Colony-stimulating factors and transferrin fusion protein by spacer optimization. Pharmacuetical Research vol. 23, No. 9, pp. 2116-2121).*

Mally Dori-BachashBacterial intein-like domains of predatory bacteria: a new domain type characterized in Bdellovibrio bacteriovorus. Funct Integr Genomics (2009) 9:153-166.*

Yue-Jin Wu Protein purification involving a unique auto-cleavage feature of a repeated EAAAK peptide. Journal of Chromatography B, 877 (2009) 4015-4021.*

Bareket Dassa,. rotein Splicing and Auto-cleavage of Bacterial Intein-like Domains Lacking a C_-flanking Nucleophilic Residue. JBC vol. 279, No. 31, Issue of Jul. 30, pp. 32001-32007, 2004.*

G. Amitai et al. Blackwell Science, LtdOxford, UKMMIMolecular Microbiology 0950-382X Blackwell Publishing, 2003. Bacterial intein-like protein domains Molecular Microbiology (2003) 47 (1), 61-73.*

Jong-Tzer Chern et al . (Chitin-binding domain based immobilization of d-hydantoinase (Journal of Biotechnology 117 (2005) 267-275).*

* cited by examiner

*Primary Examiner* — Kagnew H Gebreyesus
(74) *Attorney, Agent, or Firm* — Thomas, Kayden, Horstemeyer & Risley, LLP (57) ABSTRACT

Disclosed herein are autocleaved peptide linkers for producing purified proteins. The autocleaved peptide linkers are inserted between a chitin binding protein (CBP) and a target protein to form a fusion protein. Upon expression of the fusion protein, it is allowed to pass a chitin matrix so that the CBP portion of the fusion protein may be bound with the chitin matrix, the peptide linker then undergoes auto-cleavage in a buffer solution at a pH value of about 5.5-7.5 to release the target protein. The chitin matrix may be regenerated with another buffer solution at a pH value of about 3-4, that is, to release the bound CBP and return to its unbound form. The chitin matrix may be reused for at least 6 times without losing its function.

18 Claims, 7 Drawing Sheets
(1 of 7 Drawing Sheet(s) Filed in Color)

VECTORS, METHODS, SYSTEMS AND KITS FOR PROTEIN PURIFICATION

TECHNICAL FIELD

This disclosure in general relates to autocleaved peptide linkers and their uses with a chitin binding protein in protein purification.

SEQUENCE LISTING

The present disclosure includes a sequence listing incorporated herein by reference in its entirety.

BACKGROUND ART

Description of Related Art

Protein purification generally requires many steps of column chromatography that typically involve ion-exchange, hydrophobic-interaction and gel-filtration separations. More sophisticated purification of protein might be achieved through an application of affinity binding on a functionalized gel such as a nickel column, glutathione-modified column, maltose-modified gel column or others. However, several drawbacks exist in current prevailing protein purification methods, for examples, fusion proteins are commonly obtained and thereby a protease-digestion is necessary to remove the fusion moiety; or a costly gel is employed for affinity binding, etc.

Accordingly, there exists in this art an improved method and/or system for producing purified proteins, which may not require protease treatments; and the improved method and/or system, is easy to use, cost-effective and may produce purified proteins in large scale without sacrificing functional activity of the target proteins.

SUMMARY

As embodied and broadly described herein, disclosure herein features autocleaved peptide linkers and their uses in protein purification. Particularly, vectors are designed to express a fusion protein, which is composed of a chitin binding protein (CBP) and a target protein, joined by an auto-cleaved peptide linkes of the present disclosure. The target protein may be purified by passing the fusion protein through a chitin matrix, and the peptide linker undergoes auto-cleavage in a buffer solution at a pH value between 5.5 to 7.5 without subjecting to any protease treatment, and thereby releasing the target protein from the fusion protein. This disclosure therefore is useful in any application where purification of a protein or peptide is desirable, such as diagnostics, research uses and industrial applications.

It is therefore a first aspect of the present disclosure to provide a vector, which includes a promoter; a first polynucleotide operably linked to the promoter and encodes a chitin-binding-protein (CBP); a second polynucleotide operably linked to the first polynucleotide and encodes a linker, which upon expression produces a peptide having an amino acid sequence selected from the group consisting of SEQ ID NO: 1, SEQ ID NO: 2, SEQ ID NO: 3 and SEQ ID NO: 4, and the peptide is capable of auto-cleavage without subjecting to a protease treatment; and a third polynucleotide operably linked to the second polynucleotide and encodes a target protein.

It is a second aspect of the present disclosure to provide a method for producing a target protein. The method includes steps of:

(a) transfecting a host cell with a vector to express a fusion protein, wherein the vector comprises:
  a promoter;
  a first polynucleotide operably linked to the promoter and encodes a chitin-binding-protein (CBP);
  a second polynucleotide operably linked to the first polynucleotide and encodes a linker, which upon expression produces a peptide having an amino acid sequence selected from the group consisting of SEQ ID NO: 1, SEQ ID NO: 2, SEQ ID NO: 3 and SEQ ID NO: 4, and the peptide is capable of auto-cleavage without subjecting to a protease treatment; and
  a third polynucleotide operably linked to the second polynucleotide and encodes a target protein;

(b) lysing the host cell to produce a crude extract of the fusion protein, wherein the crude extract has a pH value that is greater than 8;

(c) passing the crude extract through a chitin matrix; and (d) incubating and further eluting the chitin matrix with a first buffer solution at a first pH value between about 5.5 to about 7.5 to produce the target protein, wherein the target protein is purified by auto-cleavage of the linker without using the protease.

In some embodiments, the method further comprises a step (c1), which is performed after the step (c) and before the step (d): (c1) eluting the chitin matrix with a second buffer solution at a second pH value between about 3 to about 4.

In some embodiments, the first pH is between about 6 to about 7. In one example, the first pH value is about 6.0. In another example, the second pH value is about 3.6.

It is a third aspect of the present disclosure to provide a system for producing a purified target protein. The system includes:
  a vector for expressing a fusion protein, which comprises
  a promoter;
  a first polynucleotide operably linked to the promoter and encodes a chitin-binding-protein (CBP);
  a second polynucleotide operably linked to the first polynucleotide and encodes a linker, which upon expression produces a peptide having an amino acid sequence selected from the group consisting of SEQ ID NO: 1, SEQ ID NO: 2, SEQ ID NO: 3 and SEQ ID NO: 4, and the peptide is capable of auto-cleavage without subjecting to a protease treatment; and
  a third polynucleotide operably linked to the second polynucleotide and encodes a target protein;
  a host cell for expressing the fusion protein encoded by the vector; and
  a chitin matrix for purifying the target protein by a method comprising steps of:
    (a) transfecting the host cell with the vector;
    (b) lysing the host cell to produce a crude extract of the fusion protein, wherein the crude extract has a pH value that is greater than 8;
    (c) passing the crude extract through a chitin matrix; and
    (d) incubating and further eluting the chitin matrix with a first buffer solution at a first pH value between about 5.5 to about 7.5 to produce the target protein, wherein the target protein is purified by auto-cleavage of the linker without using the protease.
  wherein the chitin matrix can be regenerated by eluting with a buffer solution at a pH value between about 3 to about 4.

It is a fourth aspect of the present disclosure to provide a kit for purifying a target protein. The kit includes a vector as described above, a host cell for expressing a fusion protein encoded by the vector; a chitin matrix for binding the fusion protein; a buffer solution at a pH value between about 6 and about 7 for eluting the target protein from the chitin matrix; and description in a form of pamphlet, tape, CD, VCD or DVD on how to use the kit. In some embodiments, the chitin matrix comprises β-chitin that is made form a low cost chitin source, squid pen.

The details of one or more embodiments of the invention are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The accompanying drawings are included to provide a further understanding of the invention, and are incorporated in and constitute a part of this specification. The drawings illustrate embodiments of the invention and, together with the description, serve to explain the principles of the invention. In the drawings.

DISCLOSURE OF INVENTION

The practices of this invention are hereinafter described in detail with respect to a method and system for purifying a target protein by use of a re-usable and low cost chitin matrix. A vector is designed to express a recombinant protein (e.g., a fusion protein) containing a chitin binding protein (CBP) and a target protein, and the two proteins are joined by auto-cleavage peptide linkers thereby allowing the target protein to be purified without subjecting to any protease treatment during purification. The chitin matrix may be regenerated with an appropriate buffer solution and may be reused for at least 6 times without losing its function, hence rendering the disclosed method and system even more competitive than those in the related arts.

In the first aspect of this disclosure, a vector for expressing a fusion protein is provided. The vector comprises a promoter; a first polynucleotide operably linked to the promoter and encodes a chitin-binding-protein (CBP); a second polynucleotide operably linked to the first polynucleotide and encodes a linker, which upon expression produces a peptide having an amino acid sequence selected from the group consisting of SEQ ID NO: 1, SEQ ID NO: 2, SEQ ID NO: 3 and SEQ ID NO: 4, and the peptide is capable of auto-cleavage without subjecting to a protease treatment; and a third polynucleotide operably linked to the second polynucleotide and encodes a target protein The fusion protein herein refers to a recombinant protein expressed by the vector and composes in sequence form its N-terminal to C-terminal: CBP, an autocleaved peptide linker of this disclosure, and the target protein. Construction of DNA expression vectors are well known in the art or as described in Examples of this disclosure. For the preparation of an expressed vector, primers of various genes are designed based on principles and primer design tools known in the art. In the case of obtaining a plurality of pairs of primer candidates by using such design tools, it is preferably to select primers having high annealing efficiency in consideration of primers and other parameters such as secondary structures of the target nucleic acids. The designed primers are then amplified by use of a polymerase chain reaction (PCR) to generate the desired polynucleotide sequences, which are then cloned into a cloning vector, such as pRSET A, and the cloning vector is used to transforme an appropriate host cell, such as *E. Coli*. Any ordinary skilled person in this art may know how to select a proper vector, a promoter thereof and/or host cells for implementing this invention without undue experimentation.

As used herein, a polynucleotide is a nucleic acid, which contains essential regulatory elements such that upon introduction into a host cell, is able to direct the cellular machinery to produce translation products encoded by the genes comprising the polynucleotide. By the term "operably linked to" is meant that a polypeptide coding sequence and transcriptional and translational controlling sequences are connected in such a way as to permit polypeptide expression when the appropriate molecules (e.g., transcriptional activation proteins) are bound to the regulatory sequence.

The autocleaved peptide linker of this disclosure refers to a peptide having an amino acid sequence that is any of SEQ ID NO: 1, SEQ ID NO: 2, SEQ ID NO: 3 and SEQ ID NO: 4; or a peptide having a repeated EAAAK sequence (SEQ ID NO: 21), (EAAAK)$_n$, wherein n equals 2, 3, 4 or 5. The EAAAK linker (SEQ ID NO: 21) of the present disclosure, and the (EAAAK)$_n$ linkers (SEQ ID NOs: 1-4) of the present disclosure may be referred to generally as "EAAAK linker(s)," "(EAAAK)$_n$ linkers," or just (EAAAK)$_n$ (with the appropriate value of n) throughout the specification. Any of the described peptide linker is capable of auto-cleavage in a buffer solution having a pH value between about 5.5 and about 7.5, and the target protein is released without an aid of a protease. In one example, the peptide linker undergoes auto-cleavage in a buffer solution at a pH value of about 6 to about 7. In still another example, the pH value is about 6.0.

The term "target protein" herein refers to a molecule of interest that includes any prokaryotic or eukaryotic protein that can be expressed by a vector in a transformed host cell. Suitable target protein includes, but is not limited to, enzymes such as chitosanase, chitinase, laminaripentaose-producing-β-1,3-glucanase (LPHase), hydrolase, transferase, lyase, isomerase, methylase, endonuclease or ligase; storage proteins such as ovalbumin; transport proteins such as hemoglobin; structural proteins such as actin, myosin, collagen, elastin, α-keratin, glycoprotein and fibrous protein; immunological proteins such as antigens or antigenic determinants that can be used to prepare vaccines; blood proteins such as thrombin and fibrinogen; binding proteins such as antibodies or immunoglobulins that bind and neutralize antigens; hormones such as growth factors, somatostatin, prolactin, estrogen, progesterone, insulin, interleukins, colony stimulating factor and interferon; and synthetic proteins and peptides. In one example, the target protein is chitosanase. In another example, the target protein is chitinase. In still another example, the target protein is LPHase.

The chitin matrix herein refers to any types of chitin that is capable of binding with CBP. Examples of chitin matrix include, but are not limited to, α-chitin and β-chitin. In one example, the chitin matrix is β-chitin isolated from a low cost raw material, squid pen, which is less than US$ 1.0/kg of squid pen. Unlike α-chitin, the preparation of β-chitin is relatively more environmental friendly and involves less steps of acid/base treatments and therefore generates less waste. The chitin matrix may be formed into beads, colloids, columns, films, sponges, filters, coating or other suitable surface for use in binding CBP for purpose of isolation or purification of a target protein or analysis of the presence of a target protein in a diagnostic test. In one example, the chitin matrix is in a form of a packed column.

"Host cell" herein refers to cells that may express target proteins, CBP and/or fusion proteins and may include any known expression system in prokaryotes or eukaryotes including bacterial, yeast, insect, invertebrate, and mammalian cells including human cells. In one example, the host cells are *E. Coli*. The transformed host cells are cultured and selected in accordance with any known method, such as via nutrient and/or antibiotic selections.

According to a second aspect of this invention, a method of producing a purified target protein is provided. The method includes steps of:

(a) transfecting a host cell with the vector of this disclosure to express a fusion protein;

(b) lysing the host cell to produce a crude extract of the fusion protein, wherein the crude extract has a pH value that is greater than 8;

(c) passing the crude extract through a chitin matrix; and (d) incubating and further eluting the chitin matrix with a first buffer solution at a first pH value between about 5.5 to about 7.5 to produce the target protein, wherein the target protein is purified by auto-cleavage of the linker without using the protease.

The vector constructed by the steps described above is used to transform a host cell, such as *E. Coli*. The transformed cells are cultured and selected by any known method including, but is not limited to nutrients or antibiotics selection. A cell extract containing the expressed fusion protein is prepared by any conventional technique, such as subjecting the cells to mechanical or detergent treatment to breakdown the cell membrane and then collecting the extract by centrifugation. The resulted cell extract is characterized in having a pH value of at least 8.0. In one example, the cell extract is allowed to pass a chitin matrix, such as β-chitin prepared from squid pens, the CBP portion of the fusion protein would bind to the β-chitin matrix and form a complex. The autoclaved peptide linker, such as the peptide having an amino acid sequence that is any of SEQ ID NO: 1 to 4, inserted between CBP and the target protein would then undergo auto-cleavage in a first buffer solution at a pH value of about 5.5 to 7.5, thereby releasing the target protein, which is released from the chitin matrix-fusion protein complex and then is eluted out and collected by any conventional means. In one example, the autoclevage occurs at a pH value between 6 and 7. In another example, the auto-cleavage occurs at the pH of about 6.0.

In some embodiments, the method further comprises a step (c1), which is performed after the step (c) and before the step (d): eluting the chitin matrix with a second buffer solution at a second pH value between about 3 to about 4. In one example, the second pH value is about 3.6.

According to a third aspect of this disclosure, a system for producing a purified target protein is provided. The system includes: the vector for expressing a fusion protein constructed in accordance with afore-described embodiment of this disclosure; a host cell for expressing the fusion protein encoded by the vector; and a chitin matrix for purifying the target protein in accordance with the afore-described method of this disclosure; wherein the chitin matrix can be regenerated by eluting with a buffer solution at a pH value between about 3 to about 4. Regenerating the chitin matrix herein means to elute the chitin matrix with a buffer solution with a proper pH, such as between 3 and 4, so as to release the bound CBP from the chitin matrix, and return the chitin matrix to its unbound form. In some embodiments, the chitin matrix may be reused for at least 6 times without losing its function, such as 2, 3, 4, 5 or 6 times.

It is a fourth aspect of the present disclosure to provide a kit for purifying a target protein. The kit includes a vector as described above, a host cell for expressing a fusion protein encoded by the vector; a chitin matrix for binding the fusion protein; a buffer solution at a pH value of about 6 to about 7 for eluting the target protein from the chitin matrix; and description in a form of pamphlet, tape, CD, VCD or DVD on how to use the kit. In some embodiments, the chitin matrix comprises β-chitin, which is isolated from squid pens.

The following examples serve to illustrate certain embodiments and aspects of the present disclosure and are not to be considered as limiting the scope thereof.

EXAMPLES

1 Material and Methods 1.1 Cloning of Chitin Binding Protein (CBP)

CBP was PCR-amplified using the genomic DNA of *Serratia marcescens* as template. Primers 1 and 2 (all sequences are summarized in Table 1) were designed on the basis of the cbp of *S. marcescens* (accession number AAU88202, and was purchased from Food Industry Research and Development Institute, Hsinchu, Taiwan at a catalog number ATCC 990) with Nde I and Xho I sites (underlined) in the sequences, respectively. PCR amplification was performed using Vent DNA polymerase (NEB) for 25 cycles with the conditions set for each cycle as 94° C., 30 s for denaturation, 58° C., 30 s for annealing, and 72° C., 4 min for extension. The PCR fragment was inserted into Nde I and Xho I sites of pRSET A to form the vector of pRSET/CBP.

1.2 Construction of the Expression Vectors of CBP Fusion Protein

Several steps were involved in the construction of the expression vector of the CBP fusion protein with a linker and a genenase I recognition site. In the first step, the Nde I site in pRSET/CBP was removed by site-directed mutagenesis using primers 3 and 4 for PCR amplification; the resulting vector is designated de-NdeI-pRSET/CBP. In the second step, a genenase I cutting site and a Nde I cutting site were inserted right after the CBP gene, with which the stop code in cap was deleted simultaneously; primers 5 and 6 were designed for this purpose. Both primers were phosphorylated with T4 polynucleotide kinase before use for PCR amplification. The amplified fragments were subject to self-ligation to form pRSET/CBP-G. Various peptide linkers (all linker sequences are summarized in Table 2) can be introduced subsequently. In the case when a (EAAAK)$_5$ linker (SEQ ID NO:4) is added in pRSET/CBP-G, primers 7 and 8 were employed for backward PCR amplification. Similar to the second step, both primers 7 abd 8 were phosphorylated in advance so that the amplified DNA fragments were subject to self-ligation to give pRSET/CBP-V5G. Vectors with distinct repeated EAAAK linkers, such as (EAAAK)$_2$ (SEQ ID NO:1) (EAAAK)$_3$ (SEQ ID NO:2) and (EAAAK)$_4$ (SEQ ID NO:3), were constructed with a similar strategy using primers 9 and 10, primers 9 and 11, primers 9 and 12, respectively. A vector without the genenase I proteolytic site was also constructed using primers 13 and 14; the resulting vector was named pRSET/CBP-V5. Primers 15 and 16 were employed for vector construction without CBP. For functional evaluation of this system, the gene of laminaripentaose-producing-β-1,3-glucanase (LPHase) from *Streptomyces* matensis was inserted into Nde I/EcoR I sites; the gene of chitinase from *Bacillus cereus* was inserted into Nde I/Nco I sites, and the gene of chitosanase (CNS) from *Aspergillus fumigatus* was inserted into Nde I/Hind III sites of pRSET/CBP-V5G vector, separately, and expressed in *E. coli* BL21 (DE3). The three fusion proteins CBP-V5G-LPHase, CBP-V5G-chitinase and CBP-V5G-CNS were further purified on a β-chitin column (described below).

TABLE 1

Sequences of primers

| Primer No | Sequence (5'→3') | SEQ ID NO |
|---|---|---|
| 1 | 5'-GGAATTC<u>CATATG</u>AACAAAACTTCCCGTACC-3' | 5 |
| 2 | 5'-CCG<u>CTCGAG</u>CTCTTATTTGCTCAGGTTGAC-3' | 6 |
| 3 | 5'-GGAGATATA<u>GGG</u>ATGAACAAAAC-3' | 7 |
| 4 | 5'-GTTTTGTT<u>CATCCC</u>TATATCTCC-3' | 8 |
| 5 | 5'-CCGGGTGCGGCACACTAC<u>CATATG</u>GAGCTCG AGATCTGCAGCTGGTAC-3' | 9 |
| 6 | 5'-GATCCAACCACGTTTAGCTTTGCTCAGGTTGA CGTCGATC-3' | 10 |
| 7 | 5'-CTGCTAAAGAAGCTGCTGCTAAAGAAGCTGC TGCTAAACCGGGTGCGGCACACTAC-3' | 11 |
| 8 | 5'-CAGCTTCTTTAGCAGCAGCTTCTTTAGCAGCA GCTTCTTTGCTCAGGTTGACGTC-3' | 12 |
| 9 | 5'-GAAGCTGCTGCTAAAGAAGCTGCTGCTAAAC CGGGTGCGGCACACTACCATATG-3' | 13 |
| 10 | 5'-TTTGCTCAGGTTGACGTCCATCGC-3' | 14 |
| 11 | 5'-TTTAGCAGCAGCTTCTTTGCTCAGGTTGACGT C-3' | 15 |
| 12 | 5'-TTTAGCAGCAGCTTCTTTAGCAGCAGCTTCTT TGCTCAGGTTGACGTC-3' | 16 |
| 13 | 5'-GTAGTGTGCCGCACCCGG<u>CATATG</u>TTTAGCA GCAGCTTC-3' | 17 |
| 14 | 5'-GGAATTC<u>CATATG</u>TACAATTTGCCAAAC-3' | 18 |
| 15 | 5'-GCGATCGACGTCAACCTG<u>CTCGAG</u>GAAGCTG CTGCT-3' | 19 |
| 16 | 5'-CGATTCGACATA<u>CTCGAG</u>AGCATTCGCCTGTT GCGA-3' | 20 |

TABLE 2

Peptide linkers of the CBP fusion protein

| Linker No. | Amino Acid Sequence (EAAAK)$_n$ n = 2, 3, 4, 5 | SEQ ID NO |
|---|---|---|
| 1 | (EAAAK)$_2$<br>EAAAKEAAAK | 1 |
| 2 | (EAAAK)$_3$<br>EAAAKEAAAKEAAAK | 2 |
| 3 | (EAAAK)$_4$<br>EAAAKEAAAKEAAAKEAAAK | 3 |
| 4 | (EAAAK)$_5$<br>EAAAKEAAAKEAAAKEAAAKEAAAK | 4 |

1.3 β-Chitin Matrix Preparation

Squid pens (cartilages) were used to prepare a β-chitin matrix and column. Cartilages (50 g) were soaked in NaOH (3%, 1 L) and heated at 100° C. for 3 h. The cartilages were then thoroughly washed with water to eliminate NaOH. The cartilages were further suspended in HCl (6 M, 1 L) and kept near 25° C. for 12 h. After washing with distilled water several times to increase the pH>6, the cartilages were homogenized and sieved to diameter 0.3-0.6 mm of a β-chitin matrix, corresponding to 30-50 mesh particle size. The β-chitin matrix was kept at 4° C. for further applications.

1.4 Purification of CBP and Fusion Proteins

E. coli BL21 (DE3) served as the host strain for protein expression. A single colony bearing pRSET/CBP was inoculated into LB medium (5 mL) containing ampicillin (0.1 mg/mL) and cultured at 37° C. on a rotary shaker for 12 h. The overnight culture was then transferred into a conical flask (2 L) containing LB medium (1 L) with ampicillin (0.1 mg/mL) and IPTG at 37° C. for 15 h. The culture broth was centrifuged at 4° C. for 10 min at 7000 g. The cell pellet was resuspended in sodium phosphate buffer (10 mL, 20 mM, pH 7.0) and then subjected to cell disruption with ultrasonication. After removal of the cell debris with centrifugation, the supernatant (~10 mL) was mixed with β-chitin matrix (100 mL, Tris 50 mM, $(NH_4)_2SO_4$ 1 M, pH 8.0, 5% (v/w) 0.3-0.6 mm diameter of β-chitin) and incubated at 4° C. overnight. The resulting mixture was then packed onto a 2.5×60 cm I.D. column and washed with 250 mL of the buffer solution (Tris 50 mM, $(NH_4)_2SO_4$ 1 M, pH 8.0) as a 10-fold volume of the solid chitin matrix to remove the non-binding protein. CBP was eluted from the β-chitin matrix using 50 mL of acetate buffer (20 mM, pH 3.6) with flow rate at 2 mL/min. Each fraction of 5 mL eluent was collected. All other CBP fusion proteins, including CBP-V5G-LPHase, CBP-V5G-chitinase and CBP-V5G-CNS, were purified based on the general protocol described above. The activity of the purified enzyme was assayed by using the corresponding polysaccharide as substrate (described in the following section) and the purity was analyzed by SDS-PAGE. The protein recovery yield and the purity enhancement were calculated based on the enzymatic activity and the amount of the protein retained. The recombinant chitosanase fusion protein without CBP (i.e. V5G-CNS) was purified according to the literature.

1.5 Protein Determination

The protein content of the enzyme preparation was determined by the BCA method as described in the manufacturer's protocol (BCA-1 kit for protein determination; Sigma-Aldrich, St Louis, Mo.).

1.6 Enzyme Activity Assay

The enzymatic assay of LPHase, chitinase, and CNS were performed by using β-1,3-glucan, colloidal chitin, and chitosan as the substrate, respectively. The activities were analyzed by estimating the amount of the reducing ends of sugars using the dinitrosalicylic acid method. The standard assay was prepared by mixing 0.3 ml of polysaccharide substrate (1%) and 0.3 ml of enzyme (at a suitable dilution) and incubated for 4 h at 37° C.; 0.6 ml of dinitrosalicylic acid reagent was then added, and the resulting mixture was boiled for 15 min, chilled, and centrifuged to remove the precipitants. The resulting adducts of reducing sugars were analyzed and measured spectrophotometrically at 540 nm.

1.7 Electrospray Mass-Spectrometric (ESI-MS) Analysis

Mass spectra were recorded with a quadrupole time-of-flight mass filter (Q-TOF, Micromass, UK). This analyzer was scanned over a range 500-3000 u of mass-to-charge ratio (m/z) for protein analysis, with a scan step 2 s and an interscan 0.1 s/step.

Figure 1:
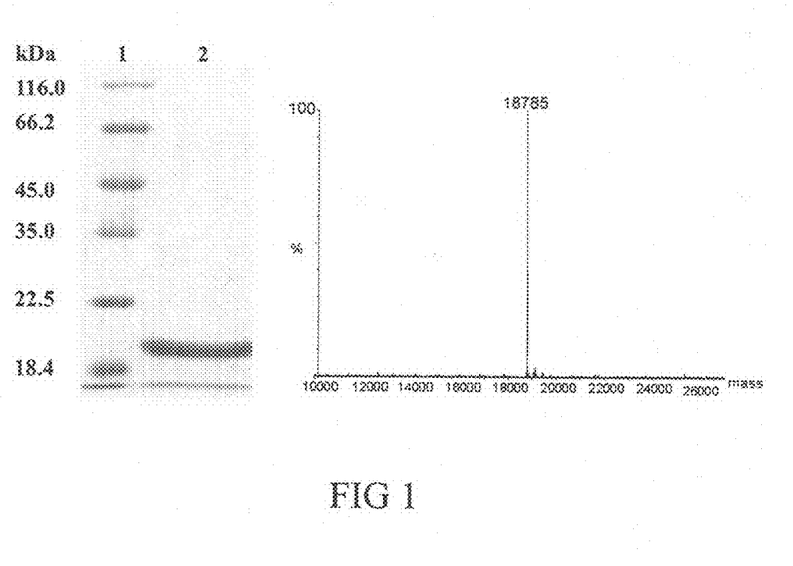
FIG. 1 illustrates the SDS-PAGE result and MS analysis of CBP. (A) Lane 1: protein marker; Lane 2: purified CBP; (B) Mass spectra of recombinant CBP.

2. Results 2.1 Cloning, Expression and Affinity-Column Purification of CBP from S. marcescens Based on the gene (cbp) of S. marcescens chitin-binding protein, two oligonucleotides were designed and used as primers for PCR cloning. With the chromosomal DNA of S. marcescens as template, a DNA fragment (0.6 kb) was amplified, and the CBP was confirmed with DNA sequencing. Sequence analysis revealed that the amplified CBP gene contained an open reading frame of 594 bp encoding 197 amino-acid residues with the first 27 amino acids as a signal peptide. The full CBP gene was further subcloned into pRSET A. The resulting plasmid was transformed into the E. coli BL21 (DE3) strain for protein expression. The recombinant enzyme, expressed as a soluble form, was further purified to high homogeneity with a β-chitin matrix. To investigate the binding affinity of CBP toward chitin, the crude recombinant protein was mixed with suitable amount of chitin matrix and further loaded onto a column and extensively washed with NaCl (50 mM) before elution with various buffers under varied pH conditions (pH 4-8), that included NaOAc (50 mM, pH 4-5), phosphate (50 mM, pH 6-7) and Tris-HCl (50 mM, pH 7-8). The eluted samples were further analyzed with SDS-PAGE. The results showed that CBP was effectively eluted from the β-chitin column when the pH was less than 7. SDS-PAGE analysis revealed that the recombinant CBP was obtained with a high homogeneity (>90%) (FIG. 1, left panel). The estimated molecular mass is ~20 kDa. ESI-MS analysis gave a more precise measurement, a molecular mass 18785 Da (FIG. 1, right panel), consistent with a theoretical calculation of the deduced protein without the signal peptide.

Figure 2:
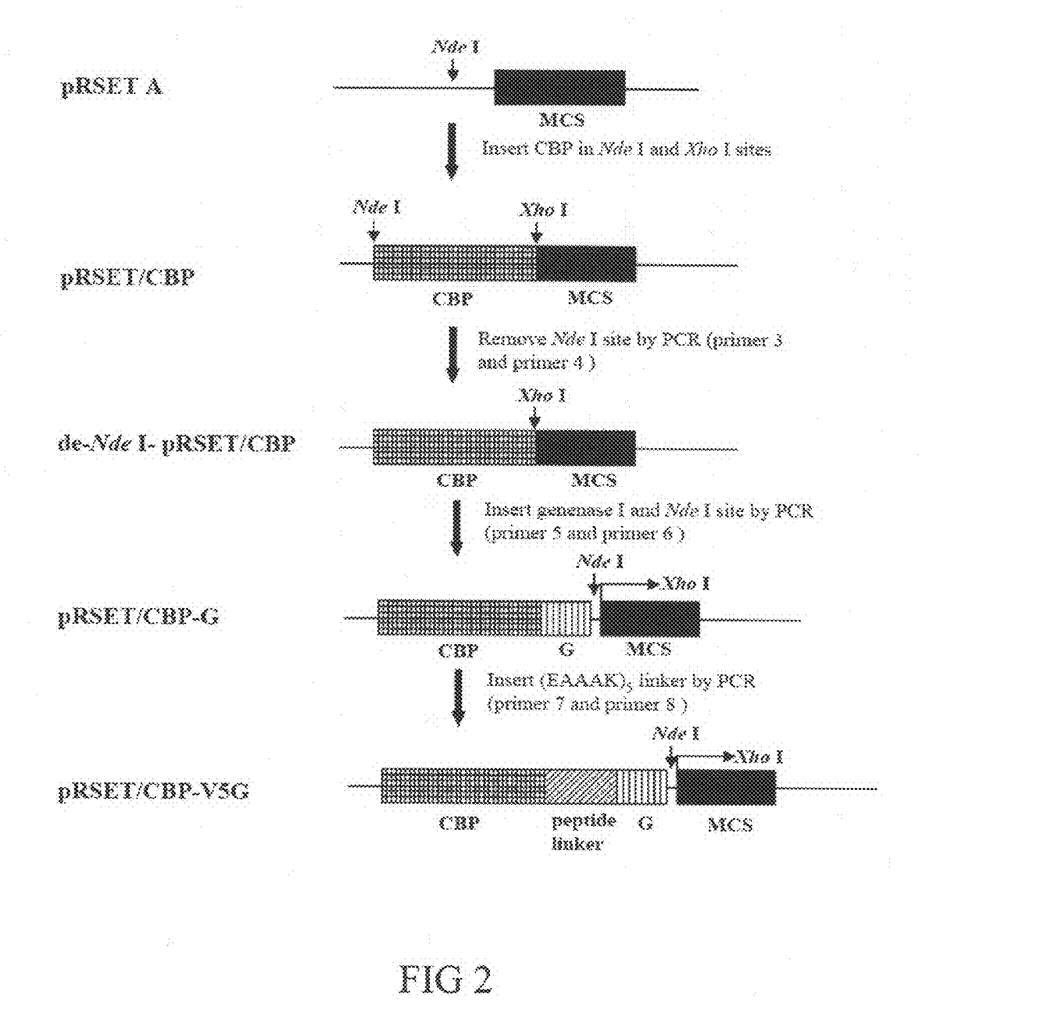
FIG. 2 illustrates the steps in constructing pRSET/CBP-V5G vector. Note that V5G represents a peptide with 5-time repeated EAAAK [i.e. (EAAAK)$_5$] (SEQ ID No: 4) following by the peptide for genenase cutting site.

The expression vector was constructed based on pRSET A. The process of plasmid construction is illustrated in FIG. 2. First, the amplified cbp was inserted in Nde I and Xho I sites. The Nde I cutting site in the resulting vector was further removed to give a plasmid designated de-NdeI-pRSET/CBP, in which the sequences of various peptide linkers and a genenase I cutting site (PGAAHY) were inserted after cbp. For further incorporation of a target gene, the Nde I site was reinserted after the genenase I site. The resulting plasmid was ready for various insertions of genes. To evaluate the feasibility of this expression vector, a tested target protein, such as chitosanase (CNS), was inserted. The proteolytic accessibility of the genenase I and the chitosanase activity of the fusion protein served as criteria to evaluate the feasibility of a linker; such as those peptide linkers shown in Table 2. Among the tested linkers, fusion proteins with $(EAAAK)_5$ (SEQ ID NO:4), GTGGEGPGGGGPGEGGTGGTGGEGPGG (SEQ ID NO: 22) or $(GGGGS)_5$ linker (SEQ ID NO: 23) (data for the last two linkers are not shown) showed significant chitosanase activity. Also, all three fusion proteins could be purified with the chitin column, and further released chitosanase (~25 kDa) after being treated with genenase I (data not shown), indicating that the peptide linkers did not perturb the structures of both proteins and that the specific proteolytic site was accessible in the fusion protein. As the $(EAAAK)_5$ (SEQ ID NO:4) peptide was known to form a helical structure and gave a yield and purity better than the other two fusion proteins after chitin-column chromatography, we selected it as the linker for our further work; the vector is designated pRSET/CBP-V5G.

Figure 3:
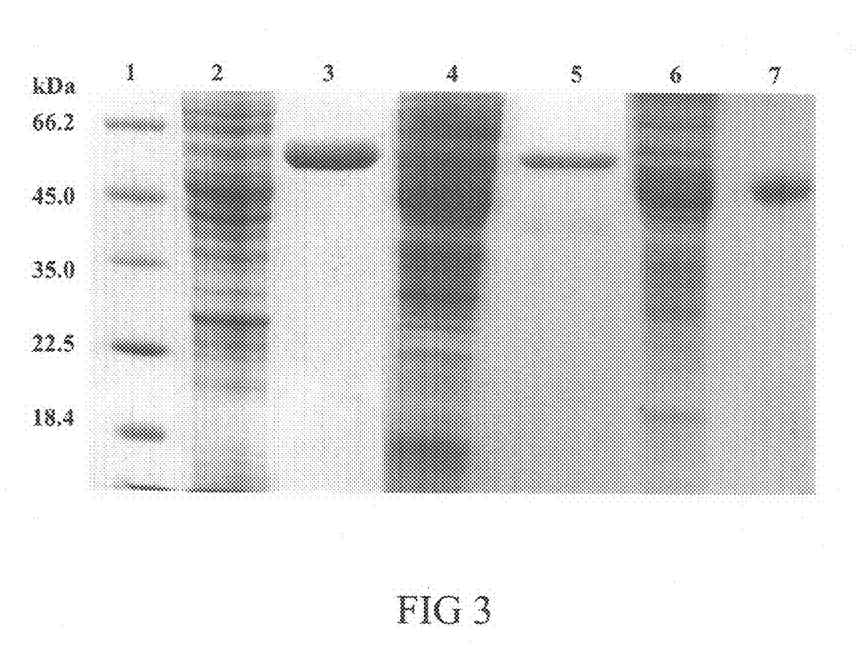
FIG. 3 is the SDS-PAGE analyses of the 3 purified recombinant fusion proteins, which respectively include laminaripentaose-producing-β-1,3-glucanase (LPHase) from *Streptomyces matensis*, chitosanase (CNS) from *Aspergillus fumigatus* and chitinase from *Bacillus cereus*. Lane 1: protein marker; Lane 2: CBP-V5G-LPHase crude enzyme; Lane 3: CBP-V5G-LPHase pure enzyme (MM 65 kDa); Lane 4: CBP-V5G-chitinase crude enzyme; Lane 5: CBP-V5G-chitinase pure enzyme (MM 58 kDa); Lane 6: CBP-V5G-CNS crude enzyme; Lane 7: CBP-V5G-CNS pure enzyme (MM 45 kDa).

To verify the function of this vector, we tested another two proteins, chitinase from Bacillus cereus, and LPHase from Streptomyces matensis for over-expression in E. coli. The fusion proteins, expressed in soluble form, were further purified to high homogeneity through the application of a chitin column as described previously. The unique characteristic of the interaction between the chitin-binding protein and the chitin matrix allows us to construct a versatile system for affinity purification of a recombinant protein. The system provides a simple and rapid way to purify a large quantity of fusion protein. The yield of purification and purity enhancement were 27% and 53-fold, 29% and 30-fold, and 58% and 137-fold for the fusion proteins of LPHase, chitinase, and chitosanase, respectively. SDS-PAGE analysis revealed that highly homogenous proteins (>90%) were obtained (FIG. 3). The fusion proteins were then subject to proteolytic cleavage with genenase I to release the recombinant enzymes (data not shown). Because of the presence of the Nde I site, the recombinant protein obtained after genenase I treatment is expected to contain an extra histidine residue at the N-terminus.

2.2 Control of the Acid-Dependent Auto-Cleavage of $(EAAAK)_5$ Linker

Figure 4:
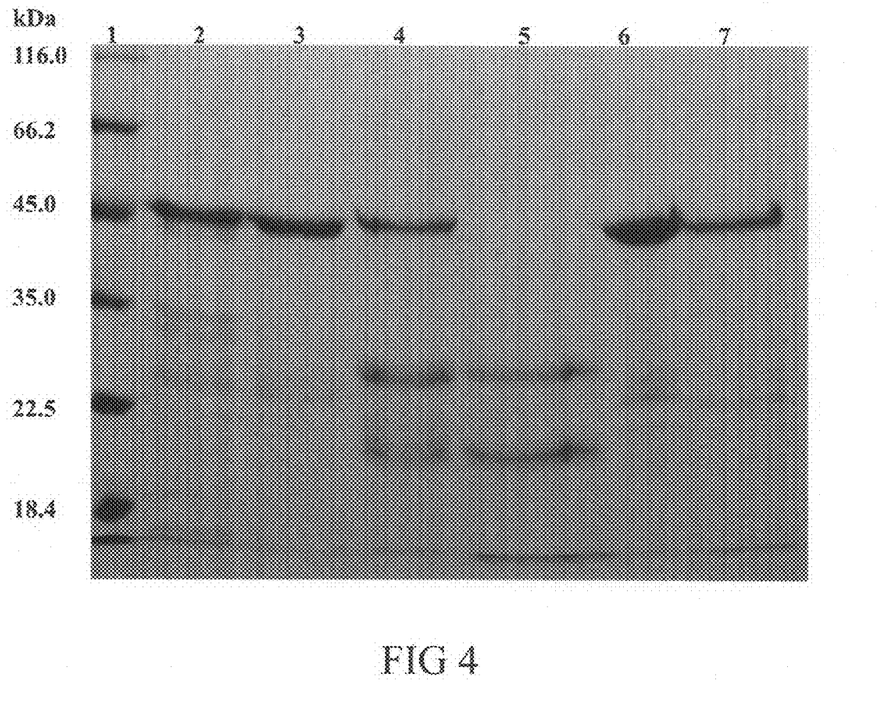
FIG. 4 is the SDS-PAGE analyses of CBP-V5G-CNS fusion protein at varied pH to test auto-cleavage. Lane 1: protein marker; Lane 2: Tris, pH 8.0; Lane 3: Tris, pH 7.5; Lane 4: phosphate, pH 7.0; Lane 5: phosphate, pH 6.0; Lane 6: NaOAc, pH 5.1; Lane 7: NaOAc, pH 4.2. Note that, in Lane 5, the upper band and the lower band are presumable to be the CNS and CBP, respectively. The band at 45 kDa is the intact fusion protein.

The striking finding of the auto-cleavage of $(EAAAK)_5$ linker (SEQ ID NO:4) was derived from a study of the optimization conditions for fusion protein elution. The binding affinity of CBP toward β-chitin depends on pH; at pH<7, CBP loses its binding affinity on chitin. In a preliminary work it was discovered that, when CBP-V5G-CNS fusion protein, derived from the expression of vector pRSET/CBP-V5G-CNS, was incubated with phosphate buffer (pH 6-7, 25° C.) for 12 h, a substantial amount of CNS was released from the fusion protein spontaneously without genenase I treatment. This unexpected cleavage might be due to contamination with a trace proportion of protease; to test this possibility, we purified the CBP-V5G-CNS protein with a chitin column with the eluent condition at pH 3.6, such that the recombinant protein remained as the original fused form of protein. This fusion protein was then heated at 100° C. for 10 min under pH 3.6. The resulting sample was subjected to exchanging buffers with pH 4.2-8.0 and then kept at 25° C. for 12 h. SDS-PAGE analysis (FIG. 4) showed that the feature of auto-cleavage of fusion protein was retained, and that the auto-cleavage occurred exclusively within pH 6.0-7.0. The best effect was observed at pH 6.

2.3 Analysis of Auto-Cleavage of Fusion CNS with Various Repeated EAAAK Linkers

Figure 5:
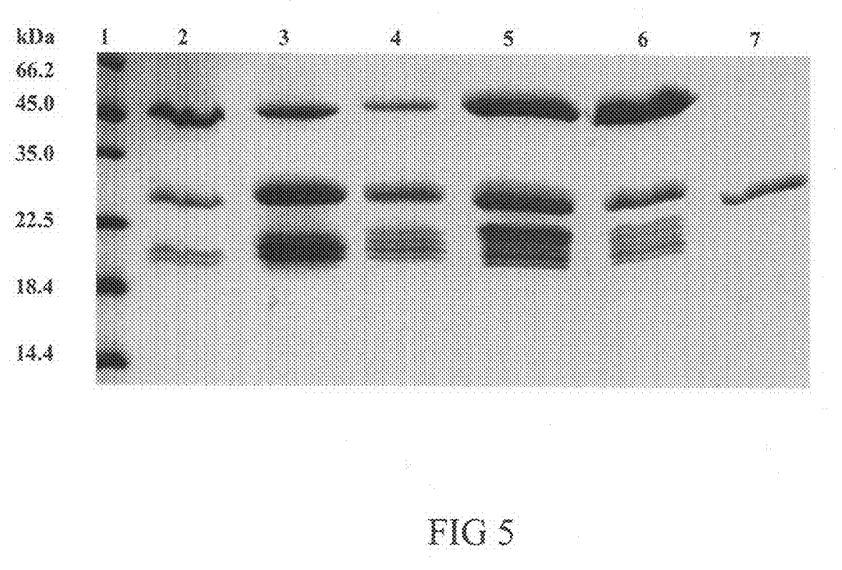
FIG. 5 is the SDS PAGE analyses of linkers' auto-cleavage. The fusion proteins were incubated in phosphate buffer (pH 6.0 at 16° C.) so that partial auto-cleavage was obtained. Lane 1: protein marker. Lane 2: CBP-V2G-CNS; Lane 3: CBP-V3G-CNS; Lane 4: CBP-V4G-CNS; Lane 5: CBP-V5G-CNS; Lane 6: CBP-V5-CNS (protein expressed without the peptide sequence of the genenase I cutting site); Lane 7: V5G-CNS (protein expressed without CBP)

To understand the detailed auto-cleavage feature, varied repeat units, $(EAAAK)_n$ with n=2, 3, 4, 5, (i.e., SEQ ID NO: 1 to 4, respectively) were introduced in the fusion protein. Sufficient fusion protein was purified and subjected to auto-cleavage assessment. All these fusion proteins were incubated at 16° C. in a phosphate buffer (100 mM, pH 7.0) containing NaCl (300 mM) for 12 h. Under these conditions, the auto-cleavage of fusion protein was incomplete. As shown in FIG. 5, the SDS-PAGE analysis revealed a systematic pattern of protein bands for all fusion proteins. The protein ladder near 20 kDa might result from a separate degree of cleavage of the repeated EAAAK linker. For instance, after partial auto-cleavage, the fusion protein CBP-V2G-CNS (Lane 2 in FIG. 5) exhibited four clear bands, showing with the estimated molecular masses 45, 26, 20 and 19 kDa, which presumably correspond to the intact fusion protein, the PGAAHY-CNS (PGAAHY is SEQ ID NO: 24) (CNS fusion protein with genenase I recognition site), CBP-$(EAAAK)_2$, and CBP-EAAAK, respectively. Similarly, for the case of CBP-V3G-CNS, the five protein bands shown from large to small molecular mass were expected to be the intact fusion protein, CNS linked with PGAAHY (SEQ ID NO: 24), CBP with $(EAAAK)_3$ (SEQ ID NO: 2) (CBP-$(EAAAK)_3$), CBP with $(EAAAK)_2$ (SEQ ID NO: 1) (CBP-$(EAAAK)_2$), and CBP with EAAAK (SEQ ID NO: 21) (CBP-EAAAK), respectively. Other fusion proteins with longer linkers demonstrated the same auto-cleavage pattern. We further removed either the peptide sequence of the genenase I cutting site or the CBP from the fusion protein and tested the auto-cleavage feature of the proteins. The results showed that, without the existence of the CBP portion or the recognition peptide fragment of genenase I in the fusion protein, the $(EAAAK)_5$ linker was still susceptible to auto-cleavage at pH 6.

Figure 6:
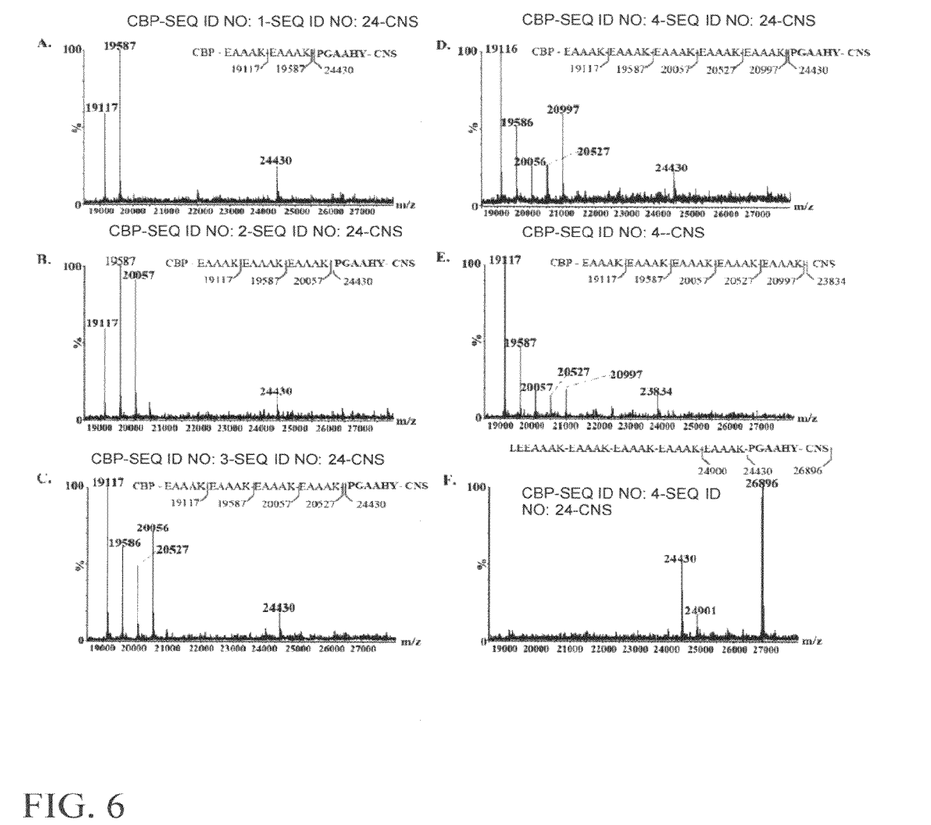
FIG. 6 is the ESI-MS analyses of fusion proteins after auto-cleavage. The samples used for mass analyses were those for SDS-PAGE analyses shown in FIG. 4. (A) CBP-V2G-CNS, (B) CBP-V3G-CNS, (C) CBP-V4G-CNS, (D) CBP-V5G-CNS, (E) CBP-V5-CNS, (F) V5G-CNS. The molecular mass (MM) of the EAAAK peptide (SEQ ID NO: 21) is 470 Da.

The suggested auto-cleavage pattern of the repeated EAAAK linkers in the fusion proteins was further confirmed with ESI/MS analyses (FIG. 6). The calculated molecular masses of CBP-$(EAAAK)_5$, CBP-$(EAAAK)_4$, CBP-$(EAAAK)_3$, CBP-$(EAAAK)_2$, CBP-$(EAAAK)_1$ are 20996, 20526, 20056, 19586 and 19115 Da, respectively, whereas PGAAHY-CNS has 24430 Da. As shown in FIG. 6, the m/z signals in each spectrum correlate well with the expected CBP-$(EAAAK)_n$ portion and the PGAAHY-CNS. For the CBP/CNS fusion protein, to cleave at the EAAAK unit adjacent to CNS seems more efficient because there was no EAAAK-linked CNS observed with ESI-MS analysis throughout the reaction. The linker continued to be cleaved from the CBP-$(EAAAK)_n$ portion, releasing a unit of (EAAAK) peptide (molecular mass 470 Da) at a time. Although the mechanism of the auto-cleavage is unclear, it is hypothesized the auto-cleavage is likely chemically controlled without an involvement of protease digestion.

2.4 Protein Purification Using the CBP System of this Disclosure

The plasmid containing CBP, the EAAAK linker of this disclosure and LPHase of *Streptomyces* matensis or the plasmid containing CBP, the EAAAK linker of this disclosure and chitosanase of *Aspergillus fumigatus* were constructed in accordance with the procedures described above. The two plasmids were then used to transfect *E. Coli* so as to produce the fusion proteins of CBP-$(EAAAK)_5$-LPHase and CBP-$(EAAAK)_5$-chitosanase, respectively.

The fusion proteins were respectively isolated and loaded into the β-chitin column prepared in accordance with the method described above, and the column was subsequently incubated and further washed with a buffer solution with a pH value of 6.0. The eluted portions were collected and analyzed with SDS-PAGE, and the results are illustrated in FIGS. 7A and 7B.

Figure 7:
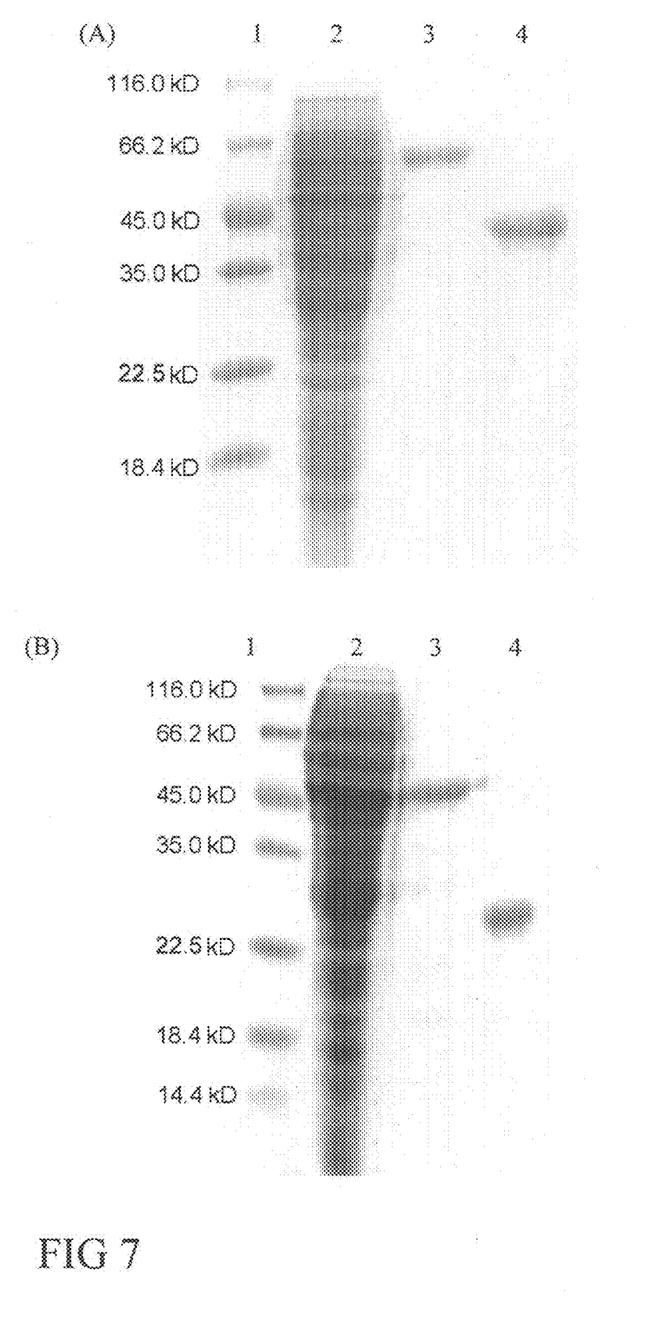
FIG. 7A is the SDS PAGE analyses of the purification of the recombinant LPHase using the CBP protein purification system of this disclosure, in which Lane 1: protein marker. Lane 2: crude enzyme; Lane 3: CBP-V5G-LPHase purified by β-chitin; and Lane 4: LPHase after auto-cleavage of the EAAAK (SEQ ID NO: 21) linker (hereinafter "EAAAK linker")
FIG. 7B is the SDS PAGE analyses of the purification of the recombinant chitosanase using the CBP protein purification system of the disclosure, in which Lane 1: protein marker. Lane 2: crude enzyme; Lane 3: CBP-V5G-CNS purified by β-chitin; and Lane 4: CNS after auto-cleavage of the EAAAK linker (SEQ ID NO: 4).

It is clear from FIGS. 7A and 7B, the CBP system of this disclosure may readily purify a target protein without the need of a protease, and purification is achieved by taking advantage of the auto-cleavage linker inserted between CBP and the target protein, the linker may undergo auto-cleavage at a slightly acidic pH and thereby release the desired target protein.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A vector for producing a fusion protein, encoded by a polynucleotide sequence, comprising:
   a promoter;
   a first polynucleotide operably linked to the promoter and encodes a chitin-binding-protein (CBP);
   a second polynucleotide operably linked to the first polynucleotide and encodes a linker, which upon expression produces a peptide having an amino acid sequence selected from the group consisting of SEQ ID NO: 1, SEQ ID NO: 2, SEQ ID NO: 3 and SEQ ID NO: 4, and the peptide being auto-cleavaging under pH value between about 5.5 to about 7.5 without subjecting to a protease treatment; and
   a third polynucleotide operably linked to the second polynucleotide and encodes a target protein.

2. The vector of claim 1, wherein the target protein is any of an enzyme, a storage protein, a transport protein, a structural protein, an immunological protein, a blood protein, a binding protein, a hormone, a synthetic protein or a peptide.

3. The vector of claim 2, wherein the enzyme is chitosanase, chitinase, or laminaripentaose-producing-β-1,3-glucanase (LPHase).

4. A method for producing a target protein, comprising:
   (a) transforming a host cell with the vector of claim 1 to express the fusion protein;
   (b) lysing the host cell to produce a crude extract of the fusion protein, wherein the crude extract has a pH value that is greater than 8;
   (c) passing the crude extract through a chitin matrix; and
   (d) incubating and further eluting the chitin matrix with a first buffer solution at a first pH between about 5.5 to about 7.5 to produce the target protein, wherein the target protein is purified by auto-cleavage of the linker without subjecting to a protease treatment.

5. The method of claim 4, further comprising a step (c1), which is performed after step (c) and before step (d): wherein step (c1) comprises eluting the chitin matrix with a second buffer solution at a second pH value between about 3 to about 4.

6. The method of claim 5, wherein the second pH value is about 3.6.

7. The method of claim 4, wherein the first pH value is between about 6.0 to about 7.0.

8. The method of claim 7, wherein the first pH value is about 6.0.

9. The method of claim 4, wherein the host cell comprises *E. Coli*.

10. The method of claim 4, wherein the chitin matrix comprises β-chitin.

11. The method of claim 10, wherein the β-chitin is produced from squid cartilages.

12. A system for producing a purified target protein, comprising:
    the vector of claim 1;
    a host cell for expressing the fusion protein encoded by the vector of claim 1; and
    a chitin matrix for purifying the purified target protein
    wherein the chitin matrix can be regenerated by eluting with a second buffer solution at a second pH value between about 3 to about 4, wherein purifying the purified target protein comprising the steps of:
    (a) transforming the host cell with the vector to express the fusion protein;
    (b) lysing the host cell to produce a crude extract of the fusion protein, wherein the crude extract has a pH value that is greater than 8;
    (c) passing the crude extract through the chitin matrix; and
    (d) incubating and further eluting the chitin matrix with a first buffer solution at a first pH between about 5.5 to about 7.5 to produce the target protein, wherein the target protein is purified by auto-cleavage of the linker without subjecting to a protease treatment.

13. The system of claim 12, wherein the host cell comprises *E. Coli*.

14. A kit for purifying a target protein, comprising:
    the vector of claim 1,
    a host cell for expressing the fusion protein encoded by the vector of claim 1;
    a chitin matrix for binding the fusion protein;
    a buffer solution at a pH between about 5.5 and about 7.5 for eluting the target protein from the chitin matrix; and
    description on how to use the kit.

15. The kit of claim 14, wherein the host cell comprises *E. Coli*.

16. The kit of claim 14, wherein the buffer solution is a phosphate buffer solution.

17. The kit of claim 14, wherein the chitin matrix comprises β-chitin.

18. The kit of claim 17, wherein the β-chitin is produced from squid cartilages.

* * * * *

SEQUENCE LISTING

<160> NUMBER OF SEQ ID NOS: 24

<210> SEQ ID NO 1
<211> LENGTH: 10
<212> TYPE: PRT
<213> ORGANISM: Artificial Sequence
<220> FEATURE:
<223> OTHER INFORMATION: Chemically synthesized linker sequence

<400> SEQUENCE: 1

Glu Ala Ala Ala Lys Glu Ala Ala Ala Lys
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Chemically synthesized linker sequence

<400> SEQUENCE: 2

Glu Ala Ala Ala Lys Glu Ala Ala Ala Lys Glu Ala Ala Ala Lys
1               5                   10                  15

<210> SEQ ID NO 3
<211> LENGTH: 20
<212> TYPE: PRT
<213> ORGANISM: Artificial Sequence
<220> FEATURE:
<223> OTHER INFORMATION: Chemically synthesized linker sequence

<400> SEQUENCE: 3

Glu Ala Ala Ala Lys Glu Ala Ala Ala Lys Glu Ala Ala Ala Lys Glu
1               5                   10                  15

Ala Ala Ala Lys
            20

<210> SEQ ID NO 4
<211> LENGTH: 25
<212> TYPE: PRT
<213> ORGANISM: Artificial Sequence
<220> FEATURE:
<223> OTHER INFORMATION: Chemically synthesized linker sequence

<400> SEQUENCE: 4

Glu Ala Ala Ala Lys Glu Ala Ala Ala Lys Glu Ala Ala Ala Lys Glu
1               5                   10                  15

Ala Ala Ala Lys Glu Ala Ala Ala Lys
            20                  25

<210> SEQ ID NO 5
<211> LENGTH: 31
<212> TYPE: DNA
<213> ORGANISM: S. marcescens

<400> SEQUENCE: 5
ggaattccat atgaacaaaa cttcccgtac c                              31

<210> SEQ ID NO 6
<211> LENGTH: 30
<212> TYPE: DNA
<213> ORGANISM: S. marcescens

<400> SEQUENCE: 6

```
ccgctcgagc tcttatttgc tcaggttgac                                    30

<210> SEQ ID NO 7
<211> LENGTH: 23
<212> TYPE: DNA
<213> ORGANISM: Artificial Sequence
<220> FEATURE:
<223> OTHER INFORMATION: Chemically synthesized primer sequence

<400> SEQUENCE: 7
ggagatatag ggatgaacaa aac                                           23

<210> SEQ ID NO 8
<211> LENGTH: 23
<212> TYPE: DNA
<213> ORGANISM: Artificial Sequence
<220> FEATURE:
<223> OTHER INFORMATION: Chemically synthesized primer sequence

<400> SEQUENCE: 8
gttttgttca tccctatatc tcc                                           23

<210> SEQ ID NO 9
<211> LENGTH: 49
<212> TYPE: DNA
<213> ORGANISM: Artificial Sequence
<220> FEATURE:
<223> OTHER INFORMATION: Chemically synthesized primer sequence

<400> SEQUENCE: 9
accgggtgcg gcacactacc atatggagct cgagatctgc agctggtac               49

<210> SEQ ID NO 10
<211> LENGTH: 40
<212> TYPE: DNA
<213> ORGANISM: Artificial Sequence
<220> FEATURE:
<223> OTHER INFORMATION: Chemically synthesized primer sequence

<400> SEQUENCE: 10
gatccaacca cgtttagctt tgctcaggtt gacgtcgatc                         40

<210> SEQ ID NO 11
<211> LENGTH: 56
<212> TYPE: DNA
<213> ORGANISM: Artificial Sequence
<220> FEATURE:
<223> OTHER INFORMATION: Chemically synthesized primer sequence

<400> SEQUENCE: 11
ctgctaaaga agctgctgct aaagaagctg ctgctaaacc gggtgcggca cactac       56

<210> SEQ ID NO 12
<211> LENGTH: 55
<212> TYPE: DNA
<213> ORGANISM: Artificial Sequence
<220> FEATURE:
<223> OTHER INFORMATION: Chemically synthesized primer sequence

<400> SEQUENCE: 12
cagcttcttt agcagcagct tctttagcag cagcttcttt gctcaggttg acgtc        55

<210> SEQ ID NO 13
<211> LENGTH: 54
<212> TYPE: DNA
<213> ORGANISM: Artificial Sequence
<220> FEATURE:
```

-continued

<223> OTHER INFORMATION: Chemically synthesized primer sequence

<400> SEQUENCE: 13
gaagctgctg ctaaagaagc tgctgctaaa ccgggtgcgg cacactacca tatg        54

<210> SEQ ID NO 14
<211> LENGTH: 24
<212> TYPE: DNA
<213> ORGANISM: Artificial Sequence
<220> FEATURE:
<223> OTHER INFORMATION: Chemically synthesized primer sequence

<400> SEQUENCE: 14
tttgctcagg ttgacgtcca tcgc        24

<210> SEQ ID NO 15
<211> LENGTH: 33
<212> TYPE: DNA
<213> ORGANISM: Artificial Sequence
<220> FEATURE:
<223> OTHER INFORMATION: Chemically synthesized primer sequence

<400> SEQUENCE: 15
tttagcagca gcttctttgc tcaggttgac gtc        33

<210> SEQ ID NO 16
<211> LENGTH: 47
<212> TYPE: DNA
<213> ORGANISM: Artificial Sequence
<220> FEATURE:
<223> OTHER INFORMATION: Chemically synthesized primer sequence

<400> SEQUENCE: 16
tttagcagca gcttctttag cagcagcttc tttgctcagg tgacgtc        47

<210> SEQ ID NO 17
<211> LENGTH: 39
<212> TYPE: DNA
<213> ORGANISM: Artificial Sequence
<220> FEATURE:
<223> OTHER INFORMATION: Chemically synthesized primer sequence

<400> SEQUENCE: 17
gtagtgtgcc gcacccggca tatgtttagc agcagcttc        39

<210> SEQ ID NO 18
<211> LENGTH: 28
<212> TYPE: DNA
<213> ORGANISM: Artificial Sequence
<220> FEATURE:
<223> OTHER INFORMATION: Chemically synthesized primer sequence

<400> SEQUENCE: 18
ggaattccat atgtacaatt tgccaaac        28

<210> SEQ ID NO 19
<211> LENGTH: 36
<212> TYPE: DNA
<213> ORGANISM: Artificial Sequence
<220> FEATURE:

-continued

<223> OTHER INFORMATION: Chemically synthesized primer sequence

<400> SEQUENCE: 19
gcgatcgacg tcaacctgct cgaggaagct gctgct                36

<210> SEQ ID NO 20
<211> LENGTH: 36
<212> TYPE: DNA
<213> ORGANISM: Artificial Sequence
<220> FEATURE:
<223> OTHER INFORMATION: Chemically synthesized primer sequence

<400> SEQUENCE: 20
cgattcgaca tactcgagag cattcgcctg ttgcga                36

<210> SEQ ID NO 21
<211> LENGTH: 5
<212> TYPE: PRT
<213> ORGANISM: Artificial Sequence
<220> FEATURE:
<223> OTHER INFORMATION: Chemically synthesized linker sequence

<400> SEQUENCE: 21

Glu Ala Ala Ala Lys
1               5

<210> SEQ ID NO 22
<211> LENGTH: 27
<212> TYPE: PRT
<213> ORGANISM: Artificial Sequence
<220> FEATURE:
<223> OTHER INFORMATION: Chemically synthesized linker sequence

<400> SEQUENCE: 22

Gly Thr Gly Gly Glu Gly Pro Gly Gly Gly Pro Gly Glu Gly Gly
1               5                   10                  15

Thr Gly Gly Thr Gly Gly Glu Gly Pro Gly Gly
            20                  25

<210> SEQ ID NO 23
<211> LENGTH: 5
<212> TYPE: PRT
<213> ORGANISM: Artificial Sequence
<220> FEATURE:
<223> OTHER INFORMATION: Chemically synthesized linker sequence

<400> SEQUENCE: 23

Gly Gly Gly Gly Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Chemically synthesized genenase recognition
      site

<400> SEQUENCE: 24

Pro Gly Ala Ala His Tyr
1               5